US00PP08550P

United States Patent [19]

Vletter

[11] Patent Number: Plant 8,550

[45] Date of Patent: Jan. 18, 1994

[54] LILY PLANT NAMED VENTOUX

[75] Inventor: Floris Vletter, Rijnsburg, Netherlands

[73] Assignee: Gebr. Vletter & J.A., Rijnsburg, Netherlands

[21] Appl. No.: 796,533

[22] Filed: Nov. 21, 1991

[51] Int. Cl.[5] ..... A01H 5/00

[52] U.S. Cl. ..... Plt./87.4

[58] Field of Search ..... Plt. 87.4

*Primary Examiner*—James R. Feyrer

*Attorney, Agent, or Firm*—Foley & Lardner

[57] ABSTRACT

A new and distinct lily plant named Ventoux, characterized by its large flowers, bicolored petals having a white main color and an intense red-purple base color which is more heavily infused in the three outer petals, long stems, vigorous growth habit, petal tips which bend downward, and its floriferous habit.

1 Drawing Sheet

The present invention comprises a new and distinct cultivar of lily, botanically known as Lilium, commercially known as Lilium asiatic hybrid, and hereinafter referred to by the cultivar name Ventoux. The parents were asiatic varieties belonging to division I described in "Classification of Lily Cultivars into Divisions" published by Victoria Mathews, The Royal Botanic Gardens, Kew (1989).

The new cultivar is a product of a planned breeding program which had the primary objectives of creating new lily cultivars with attractive contrasting bicolor flowers and other charcteristics desired for cut flower production.

The new cultivar was originated from a hybridization made by the inventor in a controlled breeding program in Rijnsburg, The Netherlands in 1984. Both the male and female parents were unnamed seedlings.

The new cultivar was discovered and selected as one flowering plant within the progeny of the stated cross by the inventor in June 1984 in a controlled environment in Rijnsburg, The Netherlands.

The first act of asexual reproduction of the new cultivar was accomplished by the inventor when scales were taken from the initial selection in 1987 in a controlled environment in Rijnsburg, The Netherlands.

Horticultural examination of selected units has demonstrated that the combination of characteristics as herein disclosed for the new cultivar are firmly fixed and are retained through successive generations of asexual reproduction.

The new cultivar has not been observed under all possible environmental conditions. The phenotype may vary significantly with variations in environment such as temperature, light intensity, and day length, without, however, any variation in genotype. The following observations, measurements and comparisons describe plants grown in Wageningen and Rijnsburg, The Netherlands under greenhouse conditions which approximate those generally used in commercial practice.

The following traits have been repeatedly observed and are determined to be basic characteristics of the new cultivar which in combination distinguish this lily as a new and distinct cultivar.

1. Large flowers.
2. Floriferous habit.
3. Bicolored flower petals comprised of a white main color and an attractive red-purple base, with the red-purple being infused more heavily in the bottom or outer flowers. There are relatively few spots or markings which are similar in color to the red-purple base.
4. Long flower stems.
5. The petal tips reflex downwardly.
6. Vigorous growth habit.

Of the many commercial cultivars known to the present inventor, the most similar in comparison to the new cultivar is Geneve, disclosed in my U.S. Plant Pat. No. 7,101. In comparison to Geneve, the new cultivar has larger flowers, a richer more intense red-purple contrasting color, and fewer spots on the flower petals. When flowering is forced under natural light, Ventoux produces an inflorescence approximately 36 days earlier than Stargazer, under the same growing conditions. Ventoux is fertile.

The accompanying photographic drawing shows typical flower characteristics of the new cultivar, with colors being as true as possible with illustrations of this type. The photograph comprises a top perspective view showing several flowers open and buds at various stages.

In the following description, color references are made to The Royal Horticultural Society (RHS) Color Chart. The color values were determined at Wageningen in 1988-1989 and Rijnsburg in July 1991.

Origin: Seedling from Breeding Program.

Parentage:

*Seed parent.*—Unnamed seedling.

*Pollen parent.*—Unnamed seedling.

Classification:

*Botanical.*—Lilium.

*Commercial.*—Asiatic hybrid.

The plant:

*Form.*—A single stem carrying numerous pedicels alternately arranged.

*Height.*—Very tall; 130 cm at time of opening of anthers of first flower.

*Growth habit.*—Vigorous and strong.

*Stem.*—Color 178A; angular in transverse section; internodal length 1 cm and uniform; anthocyanin pigment present.

*Foliage.*—Quantity: 85-100 leaves depending on growing conditions. Size of leaf: Mature leaves are of medium length (15-16 cm), and medium to narrow in width (1.5 cm). Shape of leaves: Elliptical. Texture: Smooth with weak glossiness; no pubescence. Color: Medium to dark green 137A.

*Bulbs.*—Size: Outlet 6–22 cm. Color: White.

*Roots.*—Both stem and contractile present.

The bud:

*Form.*—Tapering (like a lancet).

*Size.*—8.5 cm prior to opening.

*Opening.*—Unfolds normally.

*Color.*—161B with pink shade.

*Tepals.*—Folded, three visible.

The flower:

*Blooming habit.*—Raceme.

*Size.*—15 cm in total diameter, depending on growing conditions.

*Borne.*—Upright.

*Shape.*—Generally in form of hexagonal star; bowl-shaped in cross-section, with tips bent downwardly.

*Tepalage.*—Number of tepals: Six. Arrangement: Three inner and three outer. Color: Upper surface: Main color white 155D with red-purple base, more heavily infused in outer tepals. Lower surface: White 155D with red-purple base. Spotting or marking: Relatively few red-purple spots, 1–2 mm in diameter only at base.

*Nectaries and papillae.*—Present; weak.

*Pedicel.*—Length: 10 cm of first flower. Color: Light brown. Form: Slightly curved; tips bend downwards.

*Texture.*—Ribbed and papillose.

*Disease resistance.*—No disease problems noted to date.

*Fragrance.*—Absent.

*Lasting quality.*—Excellent.

Reproductive organs:

*Stamens, anthers.*—Arrangement: Anthers form a generally circular pattern. Length: Short to very short, 5.5 cm. Number: Six. Filaments: Green.

*Pollen color.*—Light or orange brown.

*Anther color.*—Purple.

*Pistils.*—One with green style; total length pistil 6 cm.

*Stigma.*—Brown with red-purple stigma.

*Ovaries.*—Triangular in shape other characteristics typical of asiatic lily varieties.

I claim:

1. A new lily plant named Ventoux, as illustrated and described.

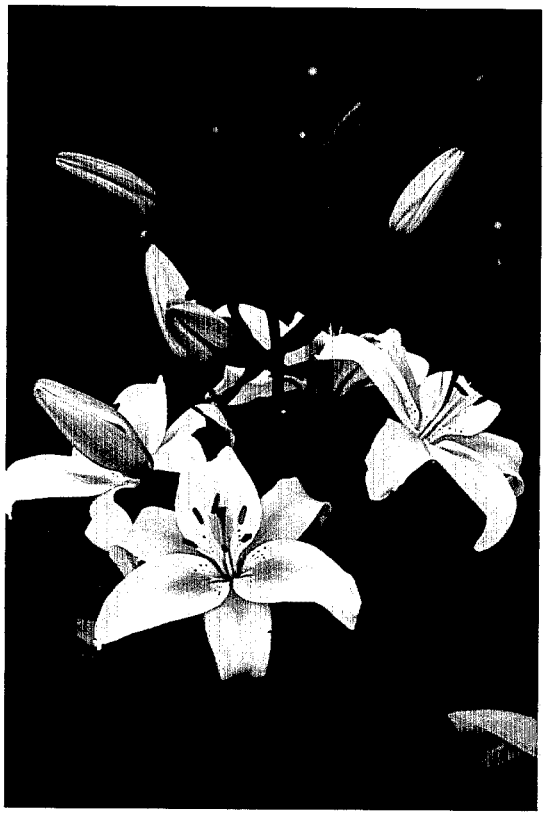

* * * * *